(12) United States Patent
Miles et al.

(10) Patent No.: US 7,034,938 B1
(45) Date of Patent: Apr. 25, 2006

(54) NON-SCANNING COMPUTED TOMOGRAPHY IMAGING SPECTROPHOTOMETER

(75) Inventors: Brian H. Miles, Niceville, FL (US); Andrew L. Hoffman, Ft Walton Beach, FL (US); Michael S. Foster, Ft Walton Beach, FL (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 677 days.

(21) Appl. No.: 10/066,511

(22) Filed: Feb. 4, 2002

(51) Int. Cl.
*G01J 4/00* (2006.01)

(52) U.S. Cl. ..................... 356/364; 356/327
(58) Field of Classification Search ........ 356/364–369, 356/327, 326
See application file for complete search history.

(56) References Cited

U.S. PATENT DOCUMENTS 5,729,011 A * 3/1998 Sekiguchi ................... 250/226
6,177,992 B1 * 1/2001 Braun et al. ................ 356/327

* cited by examiner

*Primary Examiner*—Layla G. Lauchman
(74) *Attorney, Agent, or Firm*—Richard A. Lambert (57) ABSTRACT

A Non-Scanning Computed Tomography Imaging Spectropolarimeter (NS-CTISP) measures all spatial, spectral and polarimetric information simultaneously in an image scene allowing measurement of dynamically changing scenes. In particular, NS-CTISP uses division of aperture to polarimetrically analyze each divided image, all of which are thereafter diffracted to measure irradiance on a focal plane array. The Stokes object cube data for each voxel is thereafter estimated from an inverse of the voxel polarimetric calibration matrix for the optical components.

6 Claims, 9 Drawing Sheets

NON-SCANNING COMPUTED TOMOGRAPHY IMAGING SPECTROPHOTOMETER

RIGHTS OF THE GOVERNMENT

The invention described herein may be manufactured and used by or for the government of the United States for all governmental purposes without the payment of any royalty.

FIELD OF THE INVENTION

The present invention pertains to devices that measure the spectral characteristics of a visual image, and in particular, to devices that sense the spectral composition including polarization state at each two-dimensional point in an image.

BACKGROUND OF THE INVENTION

Imaging spectropolarimeters are employed in several fields including geology, where they are used in remote sensing to locate and identify aluminum, copper, iron, lead and quartz based on their polarized reflection spectrum. Conservationists have used imaging spectropolarimeters to map polarized solar reflection from water to aid in the delineation of wetlands. In addition, imaging spectropolarimeters are widely used in astronomy in traditional settings such as telescope-based instruments, as well as airborne, rocket-borne, and satellite platforms. Mapping polarization helps astronomers to determine what physical processes created the observed light. For instance, imaging spectropolarimeters are used to locate linearly and circularly polarized atomic transitions split by the Zeeman effect induced by the large magnetic fields present in nebulae and the corona of stars. Astronomers also use imaging spectropolarimeters to study clouds on our planet as well as others.

Most imaging spectrometers perform some form of scanning to measure a Spectral Object cube (SOC). Perhaps the simplest of imaging spectrometers is a camera (e.g., film, focal plane array (FPA), etc.) with a narrowband spectral filter. This device measures a horizontal planar region in the SOC. The filtered camera relies on swapping out filters of different color to fully record the SOC. Thus, this system is said to scan in wavelength, the third dimension of the SOC, to acquire the SOC.

The filtered camera has been improved upon with high speed electronic spectral filters such as acousto-optic tunable filters (AOTFs) that can rapidly change the filter color by changing the electronic drive signal to the AOTF. This procedure can be done in tens of milliseconds, but this is unacceptable for many dynamic situations where wavelength scanning is inappropriate.

Many other imaging spectrometers require scanning in a spatial domain to acquire the SOC. For instance, a slit from an imaging spectrometer is scanned across the scene in the direction perpendicular to the slit axis. This device measures a vertical planar structure in the SOC at any given instant. The slit image is dispersed perpendicular to the slit axis by a diffraction grating onto an FPA. The information on the FPA has spatial content along the slit axis and spectral content in the orthogonal direction.

Researchers at the University of Arizona developed the Computed Tomography Imaging Spectrometer (CTIS) which can measure the entire SOC in one FPA frame via two dimensional spectral dispersion and techniques using computed tomography. CTIS is the only known device that can measure the SOC without spatial or spectral scanning.

The Computed Tomography Imaging Spectropolarimeter (CTISP), developed by Dr. Miles for his dissertation, is a polarimetric extension to CTIS. CTISP measures the spectrally dependent polarization state of the light using the Stokes vector representation of polarized light. Stokes vectors have four elements, and thus one way of visualizing the CTISP measured information is to note that CTISP measures the four Stokes Spectral Object Cubes (SSOC). The alternative is visualization in seven dimensional space (1 wavelength, 2 spatial and 4 polarization). CTISP was a proof of principle instrument that demonstrated the concept of voxel polarimetric calibration. For all its merits, CTISP relied on scanning four discrete polarization analyzers to measure the SSOCs. Thus even CTISP, which did not have to scan in the spatial or spectral domains, required polarimetric scanning.

To further understand the merits of NS-CTISP it is instructive to compare it to previously developed spectropolarimeters, most of which were developed for astronomy.

In the 1980's the University of Wisconsin developed the Wisconsin Ultraviolet Photo-Polarimeter Experiment (WUPPE) for the first ever exploration of astronomical UV polarization. WUPPE often operated as a linear polarimeter utilizing a pair of linear diode arrays to measure the Wollaston prism separated and then spectrally dispersed orthogonally polarized linear spectra. WUPPE was a competent polarimeter with an ability to measure all four Stokes parameters. For all its strengths, WUPPE provided no spatial resolution within the field of view; hence it was not an imaging device. Hence WUPPE measured a vertical column within each of the four Stokes object cubes similar to a whisk broom scanner.

The Wide-field Imaging Survey Polarimeter (WISP) was also developed by researchers at Wisconsin and is currently in use. This rocket borne device acquires wide field polarimetric images, but each image has a wide spectral band pass. WISP has two broadband filters centered at 164 and 218 nanometers. A quartet of $CaF_2$ waveplates undergoes actuator induced stress birefringence to achieve ½ wave retardance for the wavelength of interest. Thus the device has good imaging capabilities, but it integrates the polarization response over two wide wavelength regions. WISP thus measures planar structures within each of the four Stokes cubes, much like a filtered camera.

Gary Schmidt and H. S. Stockman developed a CCD Imaging/Spectropolarimeter termed SPOL. The device can measure polarization in the full instrument spectral domain (380–900 nm) for a slit source with a spectral resolution from 0.6 to 1.2 nm. The device can operate as an imaging polarimeter if a spectral bandpass filter is used. Thus this device can perform spectropolarimetry of a slit source or imaging polarimetry of an extended source but not imaging spectropolarimetry of an extended source. SPOL can be configured to acquire single wavelength band planar structures in the Stokes object cubes or a single vertical planar structure when an entrance slit is used. In either case only data from a subset of the Stokes object cubes can be acquired without scanning.

The "Advanced Stokes Polarimeter" was developed by the National Center for Atmospheric Research and the National Solar Observatory. Again although a full Stokes vector is measured, this instrument provides polarimetric information from a slit source and not an extended source, thus its limitations are similar to SPOL's.

James Hansen of the Goddard Institute of Space Studies is developing a compact instrument to study particulates on Jupiter. This device performs photometry at seven narrow spectral bands and photopolarimetry at 410, 678 and 945 nm. This device utilizes several single element detectors and thus provides no imaging capability. The device then operates much like a whiskbroom system, but even with scanning only records several narrow band horizontal planar structures within the Stokes object cubes.

Lastly, Glenar et al. describe POLARIS-II, an imaging spectropolarimeter developed at Goddard Space Flight Center. Although this device is an imaging spectropolarimeter, it only provides linear polarization information and thus not a full Stokes vector.

Clearly, a wide array of capable instruments has been developed, but none are capable of full acquisition of all Stokes object cube data in one image with no spatial, spectral or polarization scanning required. Consequently, a significant need exists for a device and method for an imaging spectropolarimeter suitable for dynamic applications unsuitable for scanning.

SUMMARY OF THE INVENTION

The invention addresses these and other problems associated with the prior art by providing an apparatus and method in which a complete polarimeter analyzer performs division of aperture on an image, polarimetrically analyzing each divided beam, and dispersing each analyzed beam into multiple diffraction orders onto a focal plane array (FPA). In the illustrative embodiment, the dispersion creates sets of diffraction orders, each set spatially separated or interleaved with the other sets. Thus, in a single imaging frame, the complete spatial, spectral, and polarization content are presented onto the FPA for full acquisition without having to scan spatially, spectrally in wavelength, or in polarization basis state. Thus, complete imaging characterization is possible even for dynamically changing images.

Consistent with one aspect of the invention, a four-faced tetrahedron prism is used for division of aperture polarization analyzing. To this end, the prismatic lens has a tetrahedron surface on one side of the optic and a single planar side on the opposing face; the four planar surfaces create four discrete beams which are each incident on one of the four different polarization analyzers.

Consistent with another aspect of the invention, a spectropolarimeter includes an input stage to collimate an image along an optical axis. The collimated image receives division of aperture by refraction into a plurality of offset beams by a four faceted prism aligned with the optical axis. Each offset beam uniquely encounters one of four polarization analyzers. The four analyzed offset beams are then incident onto a two-dimensional dispersive member, which in turn creates four sets of diffraction orders onto a focal plane array.

Consistent with an additional aspect of the invention, a method of measuring complete spectral content of an image includes collimating an image along an optical axis, performing division of aperture by refraction of the collimated image into four offset images, polarization analyzing each offset image with a selected polarization state, two dimensionally diffractively dispersing the analyzed offset images, and reimaging each analyzed offset image onto a focal plane as a set of diffraction orders.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described exemplary embodiments of the invention.

DETAILED DESCRIPTION OF THE INVENTION

The purpose of Non-Scanning Computed Tomography Imaging Spectropolarimeter (NS-CTISP) is to provide rapid and simultaneous measurement of a scene's spatially dependent spectropolarimetric exitance. NS-CTISP provides a novel imaging approach to measuring the spectral and polarimetric content of a scene while only requiring a single focal plane array (FPA) detector frame to record all the aforementioned information. NS-CTISP measures all the spatial, spectral and polarimetric information simultaneously in order to eliminate any time dependent artifacts of traditional sequential measurement techniques. Thus, NS-CTISP has tremendous advantage in any dynamic measurement scenario. From a military standpoint, rapid and simultaneous acquisition of this information provides direct time domain correlation of all the data acquired that facilitates use of multidiscriminant real time target detection algorithms.

Object Cubes

In this section, the object cube and Stokes object cubes are presented, two geometric frameworks that will be used to represent the data acquired by imaging spectrometers and imaging spectropolarimeters respectively.

Figure 1:
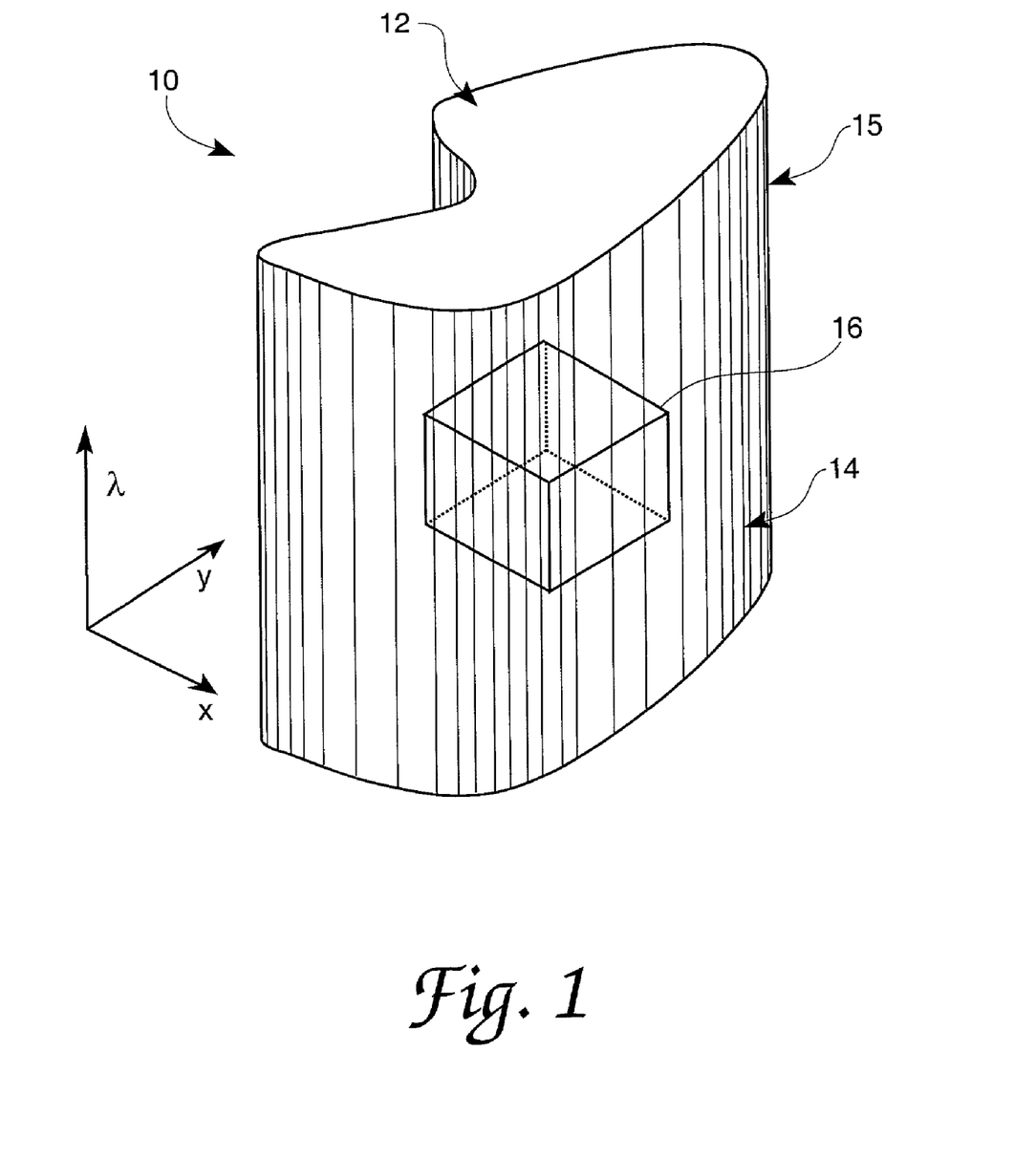
FIG. 1 is a perspective view of an object cube shown within a full spatial and spectral extent of an object image.

With reference to FIG. 1, ignoring polarization for a moment, a viewed object's spectral exitance 10 can be mathematically characterized in terms of a continuous volume x, y, λ, consisting of two spatial dimensions, x, y, and one spectral dimension λ. For completeness, the x, y extent of the volume in object space is equivalent to the projection of the object on a plane normal to the optical axis of the spectrometer, and the wavelength extent is infinite. A "kidney" shaped planar surface 12 represents the full spatial extent of the object while an infinite spectral extent is implied by vertical lines 14 to form a kidney-shaped volume 15. In reality, only a subset of this volume can be measured with a single instrument. For this reason only, a small volume 16 corresponding spatially to the x, y extent of the field of view (FOV) in object space and the spectral response of the instrument in wavelength space are considered. This subset of the object's spatially dependent spectral exitance is termed an "object cube" 16, and is seen within the larger kidney shaped volume 15.

The goal of any imaging spectrometer is to acquire an estimate of the object cube. Through the use of focal plane arrays and digital computers, modern imaging spectrometers can only represent the continuous object cube with a discrete estimate. The discrete object cube estimate then consists of a total of I by J by K elements each of volume $\delta x \delta y \delta \lambda$, where I, J and K are the total number of object cube estimate subdivisions in the x, y spatial dimensions and $\lambda$ spectral dimension, respectively. Each $\delta x \delta y \delta \lambda$ element is a small rectangular solid within the object cube estimate, and is termed a voxel. A single voxel is seen in the object cube in the left of FIG. 2. There are n=1 to N=I·J·K voxels in the object cube.

In an imaging spectrometer, a single scalar represents the exitance of each voxel. The scalar representation at each voxel accurately describes the relative spectral and spatial exitances in the FOV, but yields no information concerning the polarization state.

Figure 2:
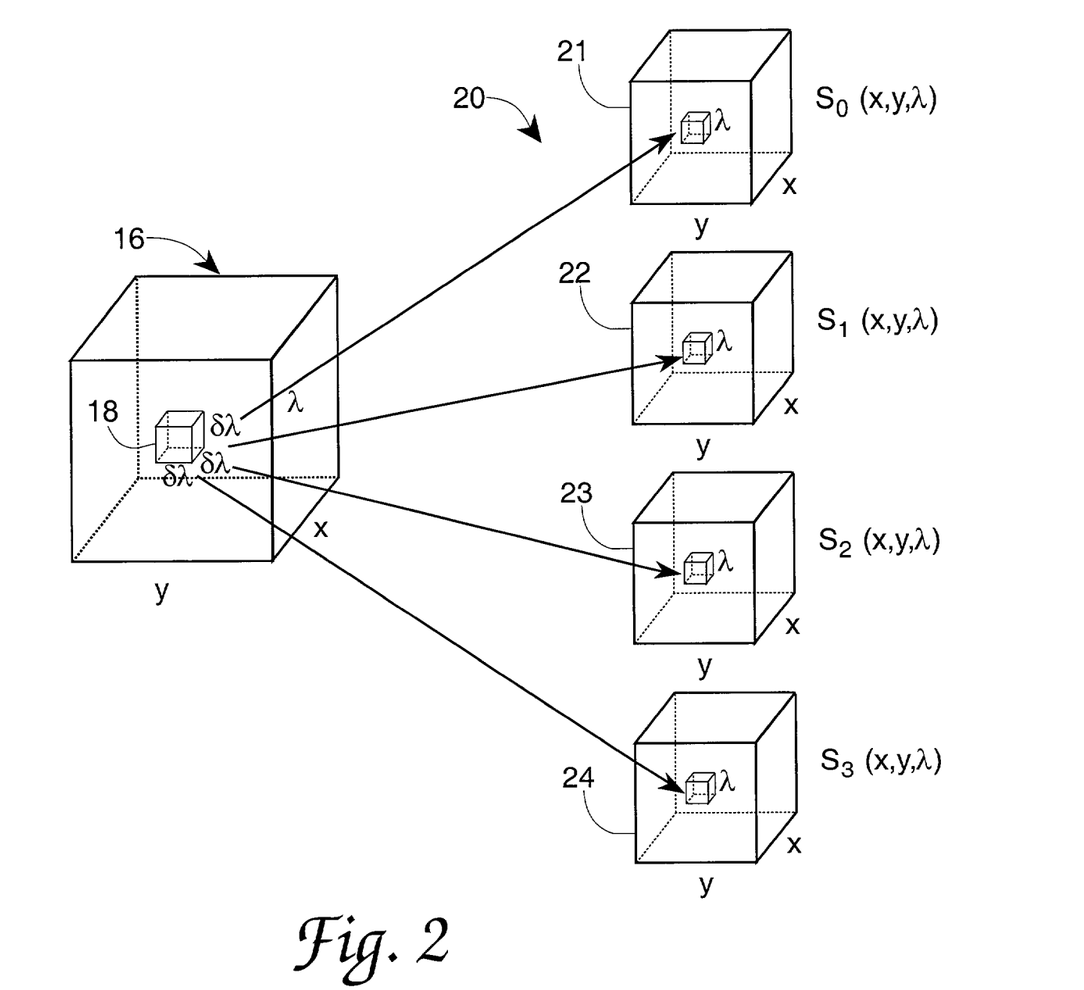
FIG. 2 is a conceptual block diagram of a Stokes spectral object cube derived from the object cube of FIG. 1.

The polarization state of partially polarized quasi-monochromatic light can be fully described using Stokes vectors, each comprised of four Stokes parameters. Thus, four Stokes parameters per voxel are needed to characterize the spectropolarimetric exitance. As indicated in FIG. 2, the role of the polarimeter in an imaging spectropolarimeter can be viewed as further dissecting a voxel in the standard object cube representation 16 into four Stokes voxels 21–24. When voxels are grouped by Stokes parameter, they form a Stokes object cube. This representation is perhaps the simplest to follow as the alternative is representation in seven dimensional (x, y, $\lambda$, $S_0$, $S_1$, $S_2$, $S_3$) space. Equivalently, a Stokes vector $\vec{S}_n$ is associated with the "nth" voxel in the object cube. The goal of an imaging spectropolarimeter is the acquisition of the Stokes object cubes.

Figure 3:
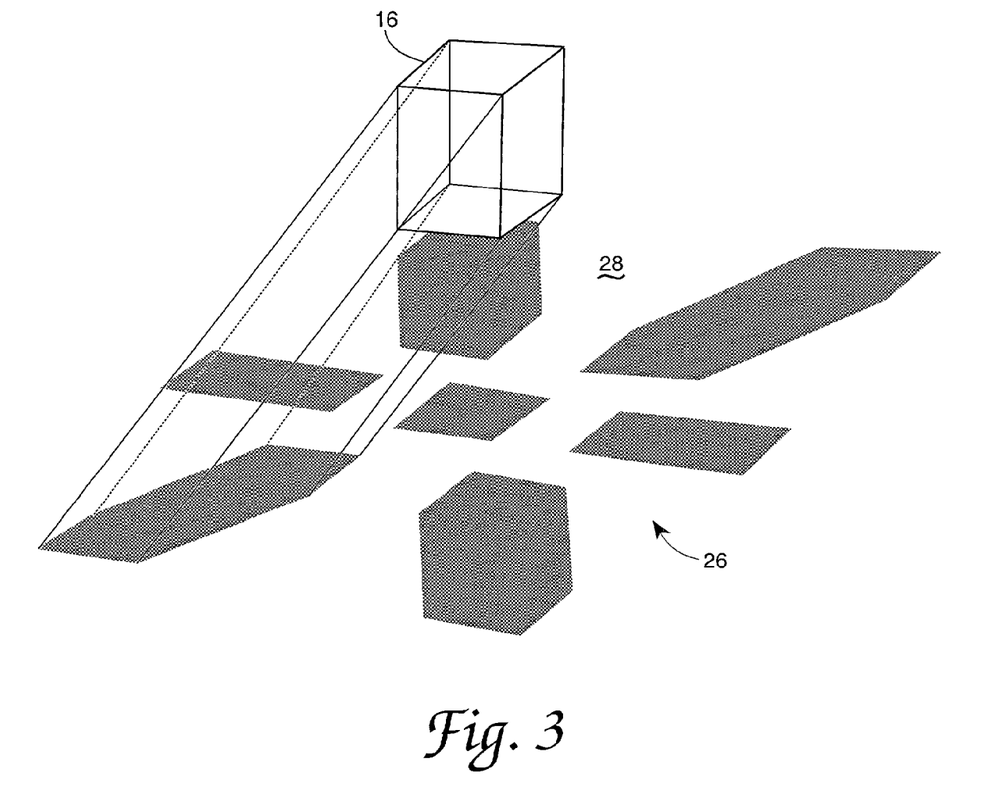
FIG. 3 is a perspective view of an object cube diffractively projected onto a focal plane.

In the model, a diffraction image can be viewed as having been produced by a plurality of projections 26 of the object cube 16 onto an FPA 28. Specifically, as shown in FIG. 3, each order corresponds to a unique projection of the object cube at a different angle. The object cube's spectral coordinate is normal to the FPA.

Optical Configuration

Figure 4:
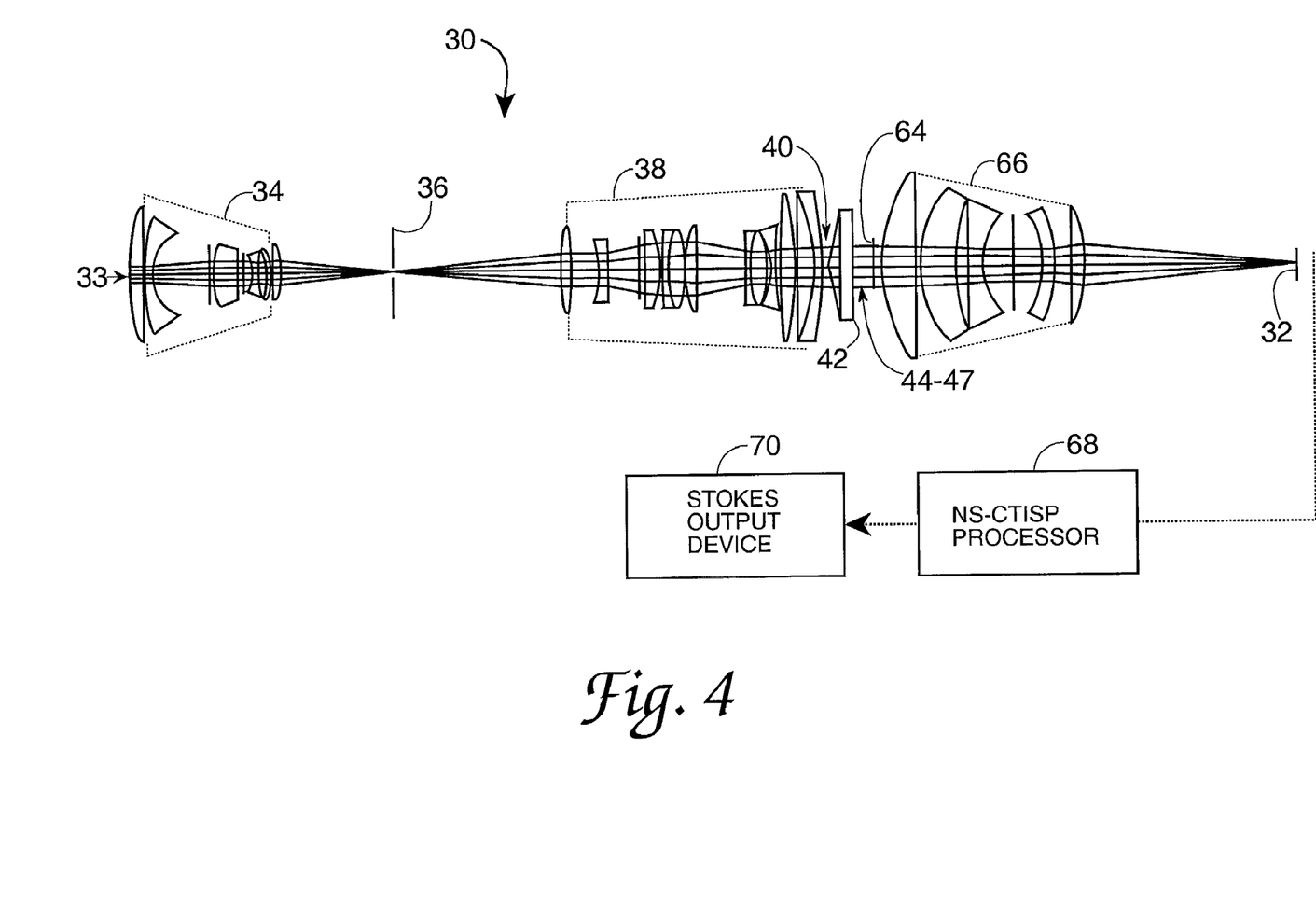
FIG. 4 is a diagram of a Non-Scanning Computed Tomography Imaging Spectropolarimeter (NS-CTISP) for finding full Stokes parameters for an unknown scene.
Figure 5:
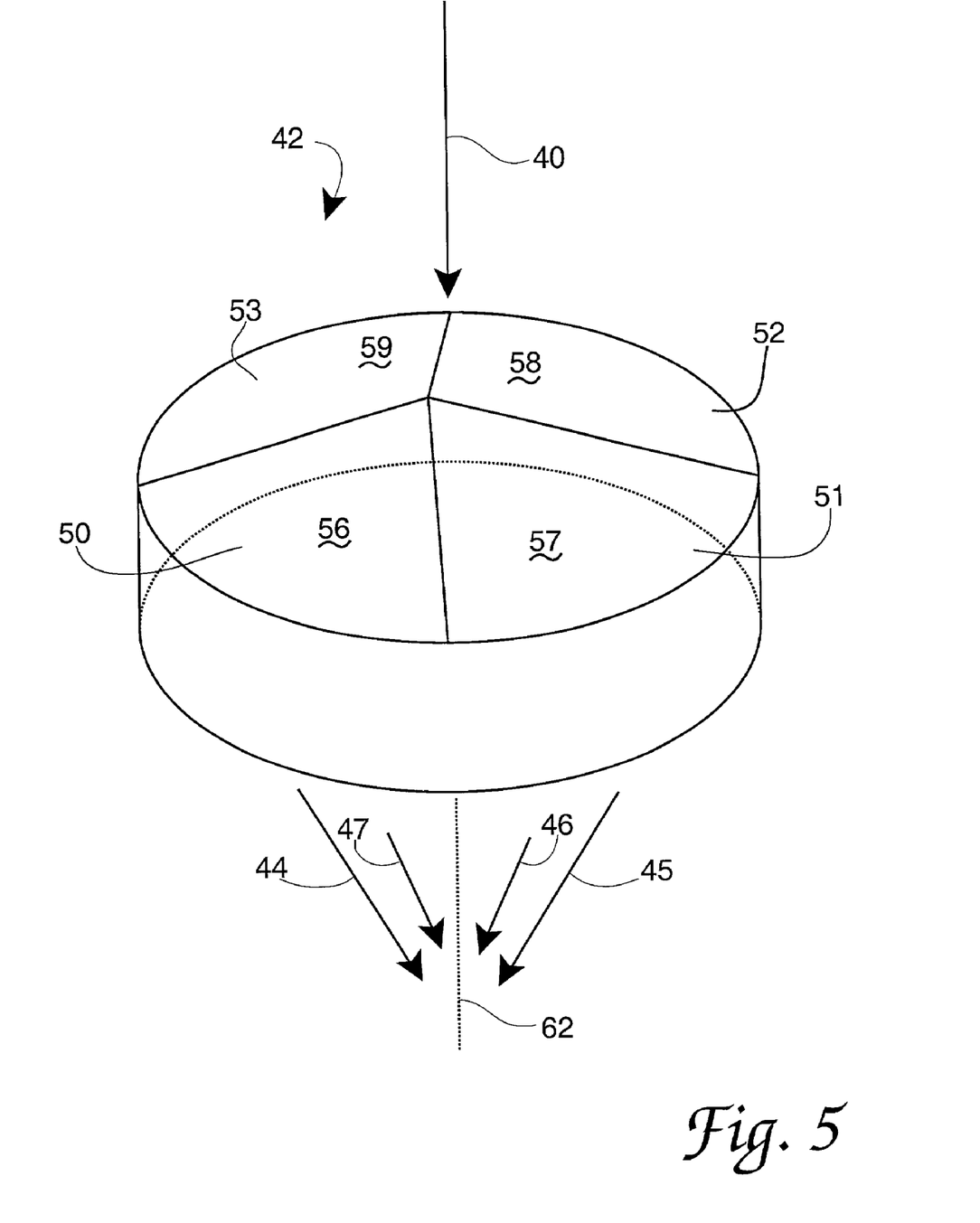
FIG. 5 is a perspective view of a tetrahedral prism of the NS-CTISP of FIG. 4.
Figure 6:
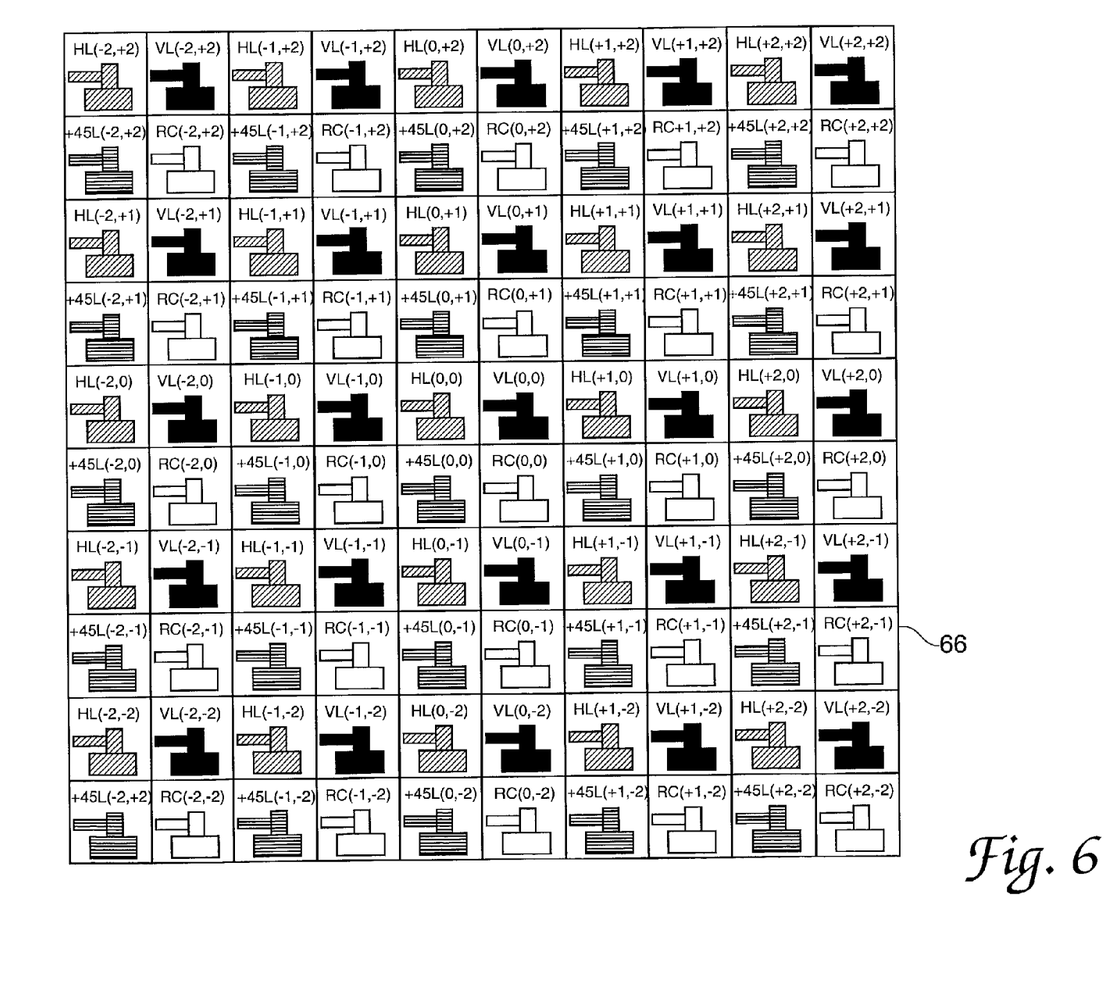
FIG. 6 is a diagram of interleaved sets of diffraction order images on a focal plane array of the NS-CTISP of FIG. 4.

With reference to FIG. 4, an illustrative NS-CTISP 30 is capable of measuring the SSOC's exitance due to its ability to separate the spatial, spectral and polarimetric content of the scene and distribute this information over the full surface of a FPA 32. Perhaps the best way to understand the NS-CTISP 30 is to describe its action on light collected from a scene. NS-CTISP 30 is designed as an imaging spectropolarimeter using a division of aperture beam separation technique. Light, as depicted at 33, enters an objective lens 34 from the left. The scene is imaged onto a field stop 36 by the objective lens 34. A collimating lens 38 is located one focal length away from the field stop 36, thus providing a collimated output beam (pupil beam) 40 to its right. With particular reference to FIG. 5, the collimated output beam 40 is incident on a tetrahedron prism 42, which then segments the pupil beam 40 into four discrete offset beams, one of the offset beams is shown by the ray set 44–47. The tetrahedron prism 42 is made of ordinary glass (BK7) and utilizes a different polarization analyzer 50–53 cemented on each entrance face or facet 56–59 to provide polarization modulation of the incoming pupil beam 40. Due to the different tilts on the four faces 56–59 of the prism 42, each beam 44–47 is refracted in a slightly different direction. All beams 44–47 are refracted toward an optical axis 62 and toward a computer generated hologram (CGH) disperser 64. The CGH 64 is a monolithic and static phase grating that is designed to disperse each of the four beams 44–47 into an array of 25 diffraction orders for a total of 100 diffraction orders on the array, as depicted in FIG. 6. It will be appreciated that the number of diffraction orders is illustrative and that more or less orders may be selected.

The CGH 64 separates the spatial and spectral content of the beam 40 while the tetrahedron prism 42 performs the polarization analysis of the beam 40.

The voxels are reconstructed by a NS-CTISP processor 70 using the algorithms and matrix formulations that follow in the mathematical description. There are four reconstructed voxel results for the same spectral and spatial voxel, corresponding to the four polarization analysis beams 44–47 from the tetrahedron prism 42. The relative intensities are fed into the voxel polarimetric calibration matrix formulation, and the resulting output on a NS-CTISP output device 70 (e.g., graphic display, alphanumeric table) is the Stokes vector for every wavelength band and every spatial resolution element that NS-CTISP responds to.

Mathematical Description of Invention

For a single exposure, NS-CTISP records four spatially separated sets of 5 order by 5 order diffraction images on the focal plane array (FPA). Each set of orders is labeled first by the polarization analyzer that it traversed (HL=horizontal linear analyzer, VL=vertical linear analyzer, +45L=45 degree linear analyzer, and RC=right circular analyzer) and each set is color coded as well. A single set of 25 diffraction orders generated through analyzer $\alpha$ is subscripted and written $\vec{g}_\alpha$. $\vec{g}_\alpha$ is formed by extracting the values from the FPA corresponding to diffraction orders produced by the aperture portion defined by analyzer $\alpha$ and has dimension M, the number of pixels in the focal plane array.

Note that the goal is the determination of $\vec{S}_n$, a set of N Stokes vectors. Clearly, this is equivalent to a 4 by N matrix of Stokes parameters. Note each column of the 4 by N matrix is the vector representation of an entire Stokes object cube.

For the purposes of polarization measurement $\vec{f}_\alpha$ also includes the analyzer subscript $\alpha$. $\vec{f}_\alpha$ represents the object cube $\vec{f}$ modified by analyzer $\alpha$, and is a 1×N vector; effectively, $\vec{f}_\alpha$ is the spectral object cube as it appears when viewed through analyzer $\alpha$. $H_\alpha$ is the response of NS-CTISP to a full set of basis voxels, when only the contribution due to analyzer $\alpha$ is recorded. Note each set of diffraction patterns generated by a different analyzer configuration $\alpha$ has its own calibration matrix $H_\alpha$. The operative relationship for multiple instrument configurations is:

$$\vec{g}_\alpha = H_\alpha \vec{f}_\alpha + \vec{\xi}_\alpha \qquad \text{Equation 1.1}$$

where $\vec{\xi}_\alpha$ represents additive system noise acquired while the system is in configuration $\alpha$.

Each column of $H_\alpha$ contains the NS-CTISP response to a voxel having a specific polarization basis state $\beta$. The term "basis state" and the variable $\beta$ indicate that the light is fully polarized and is either linearly polarized (vertically, horizontally, +45 degree, −45 degree) or right or left circularly polarized.

In order to calibrate NS-CTISP, four matrices $H_{VA}$, $H_{+45A}$, $H_{HA}$, $H_{RCA}$ must be experimentally determined. In principle, to determine these, the fiber image is translated to N positions on a rectangular 3D lattice, specified by $(\overline{x}, \overline{y}, \overline{\lambda})$, n=1, ..., N. The fiber is moved to each of these N locations and must be alternately set to four polarimetric basis states $\beta$ and the response to each of these recorded.

NS-CTISP Reconstruction Algorithm

The $\vec{f}_\alpha$ object cube is reconstructed from NS-CTISP diffraction images with the help of an iterative form of the Expectation-Maximization (EM) algorithm. The algorithm is started by setting $\vec{f}^{(0)}=1$. The expectation step computes the vector $\vec{i} = H\vec{f}^{(p)}$ based on the current estimate of the object cube, $\vec{f}^{(p)}$, as in Equation 1.2. Here $f_{\alpha,n}$ refers to the entire object cube as seen through analyzer $\alpha$, while $f_{\alpha,n}$ will be used to represent a single element of vector $\vec{f}_\alpha$ corresponding to voxel n. The script representations $H_{\alpha,mn}$, $g_{\alpha,m}$ also represent scalar elements of their respective matrices, $\vec{H}_\alpha$, $\vec{g}_\alpha$. With each iteration, a correction factor is calculated for every voxel. The p+1 estimate of the nth voxel's exitance as noted behind analyzer $\alpha$ in iterative form is:

$$\vec{f}_{\alpha,n}^{(p+1)} = \frac{\vec{f}_{\alpha,n}^{(p)}}{\sum_{m'=1}^{M} H_{\alpha,m'n}} \sum_{m=1}^{M} H_{\alpha,mn} \frac{g_{\alpha,m}}{(H_\alpha \vec{f}_\alpha^{(p)})_m} \quad \text{Equation 1.2}$$

Theoretically, the algorithm stops when the quotient $$\frac{g_{\alpha,m}}{(H_\alpha \vec{f}_\alpha^{(k)})_m}$$

reaches unity. In practice, the reconstruction process is limited to 10 iterations to minimize image noise amplification in the algorithm.

Voxel Polarimetric Calibration

The concept of polarimetrically calibrating each voxel is key to the polarimetric functionality of NS-CTISP. Since voxels are abstract subdivisions of the object cube (x, y, $\lambda$), the concept of polarimetrically calibrating each of these is a bit abstract. Nonetheless, using tools derived from computed tomography and polarimetry (and even quantum mechanics) each voxel can be polarimetrically calibrated. The goal of this section is to derive the relationships leading to the single voxel calibration matrix $W_n$.

The first objective is to derive an equation for the measured irradiance, "E'", behind an analyzer quadrant, "$\alpha$", in terms of an analyzer characteristic vector "$\vec{a}_\alpha$" and an incident Stokes vector "$\vec{S}$". A linear operator, $A_\alpha$, is introduced which operates on the electromagnetic field $\epsilon$ resulting in the field $\epsilon'$. The operator is subscripted "$\alpha$" since it will always correspond to an analyzer "$\alpha$":

$$\epsilon' = A_\alpha \epsilon \quad \text{Equation 1.3}$$

This can be recast in terms of coherency matrices:

$$J' = \langle \epsilon' \otimes \epsilon'^\dagger \rangle = \langle A_\alpha \epsilon \otimes \epsilon^\dagger A_\alpha^\dagger \rangle \quad \text{Equation 1.4}$$

where $\otimes$ indicates the Kronecker product of $\epsilon'$ with its hermitian conjugate ($\dagger$). At this point, the operator "$A_\alpha$" takes the form of a 2 by 2 matrix. Using these previous two expressions and the definition of the coherency matrix, an expression relating the input and output coherency matrices is obtained:

$$J' = A_\alpha J A_\alpha^\dagger \quad \text{Equation 1.5}$$

Since NS-CTISP does not measure the field directly, an expression that relates the input coherency matrix, the output coherency matrix, the linear operator and the measured irradiance is needed. The irradiance on a detector placed after the analyzer is calculated as the trace of the coherency matrix of the beam, or:

$$E' = Tr(J') = Tr(A_\alpha J A_\alpha^\dagger) = Tr(A_\alpha^\dagger A_\alpha J) \quad \text{Equation 1.6}$$

The last re-arrangement in the last equality is made possible by the cyclic permutation property of the trace.

At this point, a diversion into 2×2 matrix basis sets is needed. The Pauli spin matrices, derived for quantum mechanics and listed below, form a complete basis set for any 2×2 matrix.

$$\sigma_0 = \begin{bmatrix} 1 & 0 \\ 0 & 1 \end{bmatrix} \sigma_1 = \begin{bmatrix} 1 & 0 \\ 0 & -1 \end{bmatrix} \quad \text{Equation 1.7}$$

$$\sigma_2 = \begin{bmatrix} 0 & 1 \\ 1 & 0 \end{bmatrix} \sigma_3 = \begin{bmatrix} 0 & i \\ -i & 0 \end{bmatrix}$$

Fano determined the expansion of the coherency matrix in terms of the Pauli spin matrices:

$$J = \frac{1}{2} \sum_{p=0}^{3} S_p \sigma_p \quad \text{Equation 1.8}$$

The first term in the summation is, in fact, an indexed Stokes parameter. Next, returning to Equation 1.6 a general expansion is made for $A_\alpha^\dagger A_\alpha$ in terms of the Pauli spin matrices and four unknown coefficients $\alpha_{\alpha,p}$:

$$A_\alpha^\dagger A_\alpha = \sum_{p=0}^{3} \alpha_{\alpha,p} \sigma_p \quad \text{Equation 1.9}$$

The Pauli matrices have several interesting properties, one of which is a trace property using the Kronecker delta:

$$Tr[\sigma_i \sigma_j] = 2\delta_{ij} \, i=0,1,2,3; j=0,1,2,3 \quad \text{Equation 1.10}$$

Substituting Equations 1.9 and 1.8 in Equation 1.6 and utilizing Equation 1.10 the desired relationship is obtained:

$$E' = \sum_{p=0}^{3} \alpha_{\alpha,p} S_p = \vec{a}_\alpha \cdot \vec{S} \qquad \text{Equation 1.11}$$

In the case above, the irradiance measurement is made by a detector behind the analyzer. In the case of NS-CTISP, the irradiance measurement is a single voxel reconstruction result from one of the four sets of diffraction patterns. In keeping with the notation in Equation 1.2, an irradiance measurement provided by reconstruction behind an analyzer facet "$\alpha$" for a single voxel "n" is $\vec{f}_{\alpha,n}$. Furthermore, if voxel "n" is known to radiate polarization basis state "$\beta$", as is the case during calibration, then Equation 1.11 can be rewritten:

$$\hat{f}_{\alpha,\beta,n} = \vec{a}_{\alpha,n} \cdot \vec{S}_{\beta,n} \qquad \text{Equation 1.12}$$

It is important to note that for the development in this section a single voxel is being polarimetrically calibrated. The Stokes object cube vector consisting of four Stokes object cube voxels is the radiating object. These four object cube voxels share the same $(x,y,\lambda)$ coordinates which correspond to a unique voxel index "n". For this reason, the Stokes object cube of basis state "$\beta$", corresponding to a single polarized voxel of index "n", is represented by $\vec{S}_{\beta,n}$. Thus, $\vec{S}_{\beta,n}$ indicates the system is being illuminated by a voxel at location (x, y) with wavelength $\lambda$ (corresponding to voxel index n) and polarization basis state "$\beta$". Note also that $\hat{f}_{\alpha,\beta,n}$ is a scalar and refers to the reconstruction estimate of voxel "n" behind analyzer facet "$\alpha$" based on being illuminated by a single voxel of basis state "$\beta$" at voxel "n" (i.e. $\vec{S}_{\beta,n}$).

Now that the first objective has been met in Equation 1.12, it is clear that the unknown instrument characteristic coefficients $\vec{a}_{\alpha,n} = [\alpha_{\alpha,n,0}, \alpha_{\alpha,n,1}, \alpha_{\alpha,n,2}, \alpha_{\alpha,n,3}]$ must be determined. For the following example, a vertical linear analyzer facet is chosen. Substituting, Equation 1.12 now becomes:

$$f_{\alpha,\beta,n} = \vec{a}_{\alpha,n} \cdot \vec{S}_{\beta,n} \qquad \text{Equation 1.13}$$

Clearly, with one equation and four unknowns comprising $\vec{a}_{VA,n}$, more information is needed. The solution is simply to make four measurements illuminating the system with a different known polarization basis state "$\beta$" each time. For example, the instrument can be illuminated with vertical linear, +45 degree linear, horizontal linear and right circular polarized light in succession, recording the response, $\hat{f}_{VA,\beta,n}$, to each basis state "$\beta$". If the instrument is first illuminated with vertically polarized light, $\beta$=VL, then:

$$\hat{f}_{VA,VL,n} = \vec{a}_{VA,n} \cdot \vec{S}_{VL,n} \text{ where } \vec{S}_{VL,n} = \begin{bmatrix} 1 \\ -1 \\ 0 \\ 0 \end{bmatrix} \qquad \text{Equation 1.14}$$

Additional basis states radiating from voxel "n" are.

$$\vec{S}_{HL,n} \begin{bmatrix} 1 \\ 1 \\ 0 \\ 0 \end{bmatrix}, \vec{S}_{+45L,n} = \begin{bmatrix} 1 \\ 0 \\ 1 \\ 0 \end{bmatrix}, \vec{S}_{RCL,n} = \begin{bmatrix} 1 \\ 0 \\ 0 \\ 1 \end{bmatrix} \qquad \text{Equation 1.15}$$

Now illuminating with different basis states $\vec{S}_{HL,n}$, $\vec{S}_{-45L,n}$, $\vec{S}_{RCL,N}$ images $g_{VA,HL}$, $g_{VA,+45L}$, $g_{VA,RCL}$ are recorded and $\hat{i}_{VA,HL,n}$, $\hat{i}_{VA,+45L,n}$, $\hat{i}_{VA,RCL,n}$ are reconstructed, respectively. The measurement vector is defined:

$$\hat{i}_{VA,n} = [\hat{i}_{VA,VL,n}, \hat{i}_{VA,HL,n}, \hat{i}_{VA,+45L,n}, \hat{i}_{VA,RCL,n}] \qquad \text{Equation 1.16}$$

The measurement vector is a four element vector derived from four scalar radiances each reconstructed from voxel "n" behind analyzer facet "$\alpha$" illuminated with a different basis state "$\beta$". Note carefully that this script measurement vector $\hat{i}_{VA,n}$ is constructed by extracting the "nth" element from each of these four reconstructions $\hat{i}_{VA,VL}$, $\hat{f}_{VA,HL}$, $\hat{f}_{VA,+45L}$, $\hat{f}_{VA,RCL}$. Furthermore, be aware of the difference between the estimate of a vector and a vector constructed of estimates. Arranging the four basis Stokes vectors into a matrix "B" is defined as:

$$B = \begin{bmatrix} \vec{S}_{HL,n} \\ \vec{S}_{VL,n} \\ \vec{S}_{+45L,n} \\ \vec{S}_{RCL,n} \end{bmatrix} = \begin{bmatrix} 1 & 1 & 0 & 0 \\ 1 & -1 & 0 & 0 \\ 1 & 0 & 1 & 0 \\ 1 & 0 & 0 & 1 \end{bmatrix} \qquad \text{Equation 1.17}$$

Now the four equations are cast in matrix form as:

$$\hat{i}_{VA,n} = B \vec{a}_{VA,n} \qquad \text{Equation 1.18}$$

The desired form of the instrument characteristic coefficient equation is arrived at by inverting the previous relation to get:

$$\vec{a}_{VA,n} = B^{-1} \hat{i}_{VA,n} \qquad \text{Equation 1.19}$$

Note "B" must be non-singular to allow determination of the characteristic coefficients. In this manner the characteristic coefficients, $\vec{a}_{VA,n} \cdot \vec{S}_n$, for the simple vertical linear analyzer facet on voxel "n" are determined.

Returning to the general problem of characterizing an unknown Stokes vector, Equation 1.14 is restated, but now without knowledge of the incident Stokes vector. Thus, one equation exists thus far:

$$f_{VA,n} = \vec{a}_{VA,n} \cdot \vec{S}_n \qquad \text{Equation 1.20}$$

and four unknowns, $$\vec{S}_n = (S_0, S_1, S_2, S_3) \qquad \text{Equation 1.21}$$

The most straightforward solution to this problem is to acquire measurements of the unknown $\vec{S}_n$ utilizing the diffraction pattern sets from each of the four analyzer facets "$\alpha$". First each analyzer diffraction beam path set must be calibrated to determine the corresponding $\vec{a}_{\alpha,n}$'s in the same fashion as above. For example, if the linear analyzer facet diffraction pattern is used as input, the characteristic coefficients are found via the matrix/vector product:

$$\vec{a}_{HA,n} = B^{-1} \vec{f}_{HA,n} \qquad \text{Equation 1.22}$$

For simplicity the same set of basis Stokes vectors is used and thus the matrix "B" is the same matrix for each analyzer facet "α". If the same calibration procedure is performed for all diffraction pattern sets from each of the four analyzer facets then all four sets of characteristic coefficients, $\vec{a}_{\alpha,n}$, can be solved for, one set for each analyzer facet. Note a total of 16 irradiance measurements (16 reconstructions) are required to obtain the 4 unknown $\vec{a}_{\alpha,n}$'s. Stating all four equations:

$$\vec{a}_{VA,n} = B^{-1} \vec{f}_{VA,n}$$

$$\vec{a}_{HA,n} = B^{-1} \vec{f}_{HA,n}$$

$$\vec{a}_{+45A,n} = B^{-1} \vec{f}_{+45A,n}$$

$$\vec{a}_{RCA,n} = B^{-1} \vec{f}_{RCA,n} \qquad \text{Equation 1.23}$$

Using the characteristic coefficients obtained via Equations 1.23, the unknown Stokes vector can be determined via solution of the following four equations in the four Stokes parameter unknowns.

$$f_{VA,n} = \vec{a}_{VA,n} \cdot \vec{S}_n$$

$$f_{HA,n} = \vec{a}_{HA,n} \cdot \vec{S}_n$$

$$f_{+45A,n} = \vec{a}_{+45A,n} \cdot \vec{S}_n$$

$$f_{RCA,n} = \vec{a}_{RCA,n} \cdot \vec{S}_n \qquad \text{Equation 1.24}$$

Now arranging the above four equations in matrix form:

$$\begin{bmatrix} \hat{f}_{VA,n} \\ \hat{f}_{HA,n} \\ \hat{f}_{+45A,n} \\ \hat{f}_{RCA,n} \end{bmatrix} = \begin{bmatrix} \vec{a}_{VA,n} \\ \vec{a}_{HA,n} \\ \vec{a}_{+45A,n} \\ \vec{a}_{RCA,n} \end{bmatrix} \vec{S}_n = \begin{bmatrix} \alpha_{VA,n,0} & \alpha_{VA,n,1} & \alpha_{VA,n,2} & \alpha_{VA,n,3} \\ \alpha_{HA,n,0} & \alpha_{HA,n,1} & \alpha_{HA,n,2} & \alpha_{HA,n,3} \\ \alpha_{+45A,n,0} & \alpha_{+45A,n,1} & \alpha_{+45A,n,2} & \alpha_{+45A,n,3} \\ \alpha_{RCA,n,0} & \alpha_{RCA,n,1} & \alpha_{RCA,n,2} & \alpha_{RCA,n,3} \end{bmatrix} \begin{bmatrix} S_0 \\ S_1 \\ S_2 \\ S_3 \end{bmatrix}_n \qquad \text{Eqn. 1.25}$$

The voxel polarimetric characteristic matrix, $W_n$, for voxel "n" can now be defined as:

$$W_n = \begin{bmatrix} \alpha_{VA,n,0} & \alpha_{VA,n,1} & \alpha_{VA,n,2} & \alpha_{VA,n,3} \\ \alpha_{HA,n,0} & \alpha_{HA,n,1} & \alpha_{HA,n,2} & \alpha_{HA,n,3} \\ \alpha_{+45A,n,0} & \alpha_{+45A,n,1} & \alpha_{+45A,n,2} & \alpha_{+45A,n,3} \\ \alpha_{RCA,n,0} & \alpha_{RCA,n,1} & \alpha_{RCA,n,2} & \alpha_{RCA,n,3} \end{bmatrix} \qquad \text{Eqn. 1.26}$$

and simplify the previous equation to:

$$\vec{f}_{\alpha,n} = W_n \vec{S}_n \qquad \text{Equation 1.27}$$

Recall there is a $W_n$ matrix for each voxel, and these are determined experimentally as mentioned above. Once $W_n$ is obtained for each voxel, the calibration procedure is complete. Note that sixteen diffraction patterns, one for each permutation of the four basis states "β" and four instrument configurations "α", must be recorded and reconstructed to calibrate each voxel polarimetrically. Since the instrument configurations "α" are spatially multiplexed and recorded at the same time, only four FPA images, one for each basis state "β", need to be recorded. Then, in summary, once all the $W_n$'s have been determined via the calibration procedure, NS-CTISP can be used to estimate an object's spectropolarimetric exitance.

Data Acquisition

Now that the calibration is complete, NS-CTISP can be implemented in the "field" to estimate the Stokes object cubes of an unknown source. The set $\vec{g}_{VA}, \vec{g}_{HA}, \vec{g}_{+45A}, \vec{g}_{RCA}$ of measurements is now acquired by extracting each of the four sets of diffraction orders, one set from each analyzer facet "α". Each diffraction set $\vec{g}_\alpha$ is reconstructed using $H_\alpha$ to obtain $\vec{f}_\alpha$, noting that the illumination condition is not known and is assumed independent for each voxel:

$$\vec{g}_\alpha = H_\alpha \vec{f}_\alpha + \vec{n}_\alpha \qquad \text{Equation 1.28}$$

For each analyzer facet diffraction pattern set this becomes:

$$\vec{g}_{VA} = H_{VA} \vec{f}_{VA} + \vec{n}_{VA}$$

$$\vec{g}_{HA} = H_{HA} \vec{f}_{HA} + \vec{n}_{HA}$$

$$\vec{g}_{+45A} = H_{+45A} \vec{f}_{+45A} + \vec{n}_{+45A}$$

$$\vec{g}_{RCA} = H_{RCA} \vec{f}_{RCA} + \vec{n}_{RCA} \qquad \text{Equation 1.29}$$

Next, for each voxel "n" the corresponding voxel reconstruction element is extracted from each of $\vec{f}_{VA}, \vec{f}_{HA}, \vec{f}_{+45A}, \vec{f}_{RCA}$. These are then $\hat{f}_{VA,n}, \hat{f}_{HA,n}, \hat{f}_{+45A,n}, \hat{f}_{RCA,n}$. Recalling Equation 1.16 $\vec{f}_{\alpha,n}$ is now assembled for voxel "n". The Stokes vector estimate "$\hat{s}_n$" for voxel "n" is found by inverting Equation 1.27 and applying it voxel-by-voxel to yield:

$$\hat{s}_n = W_n^{-1} \hat{f} \qquad \text{Equation 1.30}$$

Equation 1.30 is very significant as it is the fundamental operating equation of NS-CTISP. A powerful relationship is now available that allows direct estimation of the Stokes vector for every voxel in the object cube given four reconstructions each derived from a reconstruction from a single set of diffraction orders corresponding to the beam that passed analyzer "α".

The Stokes vector estimate for every voxel in the object cube has been obtained. In summary, NS-CTISP is first calibrated by obtaining a voxel polarimetric calibration matrix "$W_n$" for each voxel. Estimates of unknown Stokes object cubes were then obtained by reconstructing four diffraction images "$\vec{g}_\alpha$" extracted from different regions in one FPA exposure behind four analyzer facets "α" and multiplying the $\hat{f}$ vector, assembled from the reconstructions, by the inverse of the voxel polarimetric calibration matrix "$W_n^{-1}$".

NS-CTISP Operation

NS-CTISP operation consists of NS-CTISP calibration, data acquisition and data reduction. The calibration process is discussed next.

Calibration Program

In order to determine $W_n$ for voxel "n", 16 diffraction sub-images, $\vec{g}_{\alpha,\beta n}$ one for each of the combination of instrument configuration "$\alpha$" and polarization basis state "$\beta$" must be acquired. Since the four quadrant polarization analyzer records four $\vec{g}_{\alpha,\beta,n}$ corresponding to the four "$\alpha$" in each FPA exposure, the number of calibration images or FPA exposures required to assemble all four $H_\alpha$ matricies is $i \cdot j \cdot k \cdot 4$. There are four $H_\alpha$'s that must be determined, one for each "$\alpha$" sub-image, resulting in a total of $i \cdot j \cdot k \cdot 4 \cdot 4$ diffraction sub-images. For the parameters previously mentioned $36*36*18*4*4=372,248$ $\vec{g}_{\alpha,\beta,n}$ vectors must be acquired. Currently the polarization creation and image acquisition time takes just 15 seconds per $\vec{g}_{\alpha,\beta,n}$ but based on this the total calibration time for all voxels would be 16 days! Furthermore, each of these images at full resolution is 1024×1024×16 bits, resulting in a total storage requirement of approximately 200 GB for all voxels.

In the quest to reduce the time and storage requirements of the calibration, the FOV location linear shift invariance of the diffraction images was investigated. The scalar product of a diffraction image of a voxel in the center of the FOV and a diffraction image of a voxel in the corner of the FOV was calculated and found to be 0.996. The near unity magnitude of the scalar product indicates the diffraction images are shift invariant. Utilizing the linear shift invariant nature of these diffraction images allows acquisition of the full range of spectral and polarization states at only one spatial location in the FOV. Then the data is shifted to other locations during reconstruction. This reduces the calibration time down to 18 minutes and cuts the maximum required storage to 151 Mbytes.

Further data reduction is implemented as many of the pixel values are near zero and will have a negligible impact on the reconstruction of the object cube and calculation of Stokes vectors. Therefore, all data below a threshold are set to zero and only nonzero values are stored in the output file. As a result of these measures, the size of complete calibration files is typically less than 4 MB.

Acquisition of the calibration images $\vec{g}_{\alpha,\beta,n}$ is performed in an automated fashion by a program called (ctisp). The user selects the voxel spectral separation $\delta\lambda$, the minimum wavelength, the number of wavelengths, the wavelength increment, an initial exposure time, and an output file directory. In order to calculate complete Stokes vectors under current procedures, all input polarization basis states must be recorded. Once these parameters have been selected, the procedure is started by clicking the "Acquire Calibration Images" button. The left hand side of the dialog box contains a status box that tells the user the current fiber image centroid position, polarization basis state "$\beta$", wavelength, image statistics, and current exposure time. The right of the dialog box displays the last image acquired, which is continuously updated as new images are taken. This exposure times are logged to an output file for later reference if needed.

The first task of the program is to establish communication with the NS-CTISP and calibration facility instrumentation and to perform initialization. The rotating linear polarizer in the calibration facility is rotated by a stepper motor to a position that produces vertical linear polarization. Next, the monochrometer is set to output light at a wavelength in the middle of the range of wavelengths specified by the user and an image of the fiber is acquired. This image is used to adjust the exposure time and then another image is acquired. This image is used to calculate the location of the center of the fiber image on the CCD array. The calibration facility is moved via micrometers in X and Y to center the fiber image on a binned pixel.

The acquisition of calibration images begins the monochrometer set to the shortest wavelength specified and the calibration facility set to produce RCL, by adjusting the achromatic quarter waveplate's fast axis to 45 degrees to the linear polarizer's axis.

An image is acquired with these settings. The exposure time is increased or decreased until the images use most of the dynamic range available from 16 bits (so until the max pixel is 56000<x<62500). The mean is calculated for an area of the CCD that is not illuminated by the calibration facility to get a measure of the background signal present during acquisition of the image. The background mean is subtracted from all pixels in the image, and all values below the background mean plus 1000 are set to zero. The image is saved to a file.

The achromatic quarter wave plate's fast axis is made colinear with the linear polarizer and both are rotated to +45 degrees to produce +45 linear. They are again rotated in tandem to horizontal and vertical orientations to acquire the final two images.

Next, the monochrometer wavelength is increased by $\delta\lambda$, and the exposure time is increased or decreased until the image makes good use of the dynamic range available from 16 bits. Images are again acquired with the polarization generation section set to each of the four polarization basis states. This is done "k" times until the system has been calibrated at all wavelengths.

Extracting Subimages, Calibration Binning, and H Matrix Formation

The information associated with each polarization analyzer are spatially multiplexed in one image and need to be separated to be stored in the appropriate H matrix files. The calibration images are binned to reduce computation time. The data is then stored in H matrix files. Since most pixels in calibration files are zero after thresholding, the H matrix files only store non-zero values and their x,y location. The same calibration program (ctisp) is used for this. All the files were saved with standard names relating to their wavelength and light basis state. The user must specify the directory where the files are, the starting wavelength, number of wavelengths, and the wavelength increment so the program finds the correct files. The user must also specify X binning window size, the Y binning window size, top left corner location of the zeroth order, and size of the zeroth order. These operations are performed when the "Create H Matrices" button is clicked. First, the pixels relating to each polarization analyzer are grouped together using pixel locations in the image to know which pixels to associate with each analyzer. Each "pixel" value in the output binned calibration images is the average of the intensity values in a binning window in the corresponding original calibration image. Any bin with an average value less than the threshold is set to zero in the output. Since shift invariance is assumed, the images are stored with the point source of light shifted to the top left corner of the zeroth order. Currently, most images are binned with X binning and Y binning parameters set to "4". Four H matricies are then formed. Each one is formed using only corresponding basis states and analyzers (such as +45 input basis state and the resulting +45 analyzer's image) at all calibration wavelengths. Thus, each of the H matricies has as many columns as there are wavelengths. The non-zero data from each sub-image is stored by value and location to reduce storage space.

W Inverse Program

The voxel polarimetric characteristic matrices, $W_n$, and their inverses, $W_n^{-1}$, that characterize the polarimetric response of each voxel are calculated from the calibration data by a program called (W_inverse). Recall that there are N $W_n$ matrices since there are N voxels. This program determines $W_n$ as discussed for the voxel polarimetric calibration. The user must specify the calibration directory, acquired with (ctisp) and binned with (ctisp), and an output file. The parameters that may be set are the X and Y resolution, the maximum tolerance, and the number of iterations. The X and Y resolution are currently always set to 1 because the calibration images are acquired at only one spatial location. The calculations begin when the user clicks the "Create W matricies" button. Each polarimetric characteristic matrix is inverted and the result is stored to the output file for later use in the calculation of Stokes vectors from NS-CTISP images. At this point, the calibration of the instrument is complete and image acquisition can be performed.

Data Acquisition and Reduction

Data acquisition begins by running a program termed (EM). There are three simple inputs to the program. The only variable to set is the exposure time. The "Acquire Image" button is clicked and the camera acquires the one image of the unknown scene. Next, the image is thresholded and stored to disk.

After the image is acquired, the four sub-images corresponding to the four analyzers must be separated. The binning should be set to match the binning of the calibration file the user intends to use in reconstruction, and this information was saved in the H matrix files so it is retrieved. The user must provide the names of an image file acquired with (EM), a calibration files acquired with (ctisp), W matrices created with (W_inverse), and an output file. The program produces four new files consisting of the datacubes containing the Stokes information for each polarization state. More detail on creating W matrices is in the next section.

Calculation of Stokes Vectors

The NS-CTISP calibration files contain calibration data collected through four different analyzers: HA, VA, +45A, and RCA. The data acquired with these four analyzers represent four separate $H_\alpha$ matrices designated as $H_{HA}$, $H_{VA}$, $H_{+45A}$, and $H_{RCA}$, respectively. A binned NS-CTISP image file contains binned versions of images $\vec{g}_{HA}$, $\vec{g}_{VA}$, $\vec{g}_{+45A}$, and $\vec{g}_{RCA}$ (EM) performs a reconstruction using each of these binned images and its corresponding binned H$\alpha$matrix. When these reconstructions are completed, the values obtained are combined to form the 4×1 vector, $\vec{f}_1$, for each voxel. The set of $W_n^{-1}$ matrices is provided by (W_inverse), and the Stokes vector for each voxel is then calculated by equation 1.30, which for convenience is repeated as follows:

$$\vec{s}_n = W_n^{-1} \vec{f}_n \qquad \text{Equation 1.30}$$

Input files required by this program include an image file acquired and binned with (EM), calibration files acquired and compressed with (ctisp), and a W inverse file that is calculated from the calibration files by the program (W_inverse). (EM) also requires four parameters to be set by the user. These are X resolution, Y resolution, maximum tolerance, and maximum iterations.

The X and Y resolutions are simply the number of binned resolution elements in the FOV. In the dialog box example there are 124 FPA pixels in the FOV, and "X binning" and "Y binning" in both (ctisp) and (EM) are set to 4 yielding 124/4=31 binned resolution elements.

The tolerance, $\Delta \hat{f}_\alpha^{(k)}$, is defined as the voxel averaged iteration-to-iteration difference in the reconstruction result for a given $\vec{g}_\alpha$ at which the EM algorithm is asked to quit. The change in $\hat{f}_\alpha$ from the previous iteration is defined as:

$$\Delta \hat{f}_\alpha^{(k)} = \frac{\sum_{n=1}^{N} \left| \hat{f}_{\alpha,n}^{(k)} - \hat{f}_{\alpha,n}^{(k)} \right|}{N}$$

When this value goes below a user-defined tolerance or when the maximum number of iterations has been completed, no more iterations are performed for that reconstruction. These values are extracted directly from the calibration file and are displayed to ensure the correct calibration file is being implemented for the given image file.

The program produces two output files. One of these, which is input in the dialog box, is a targa format image file which will contain a mosaic of Stokes parameter images upon program completion. The mosaic has 4 image columns and a number of image rows equal to the number of spectral bands or "Wave Steps". Each of the four image columns within an image row corresponds to a different Stokes parameter. In this way, an estimate of all of the data contained in the four Stokes object cubes is presented. If the images from a single column are "stacked", a Stokes object cube for that Stokes parameter results.

The other output file, which is created with the same name but a different extension (.log), records the results of each reconstruction and the Stokes vector calculations in decimal format. When the files and parameters are specified, the user clicks the "Go" button to begin the calculations.

Figure 7:
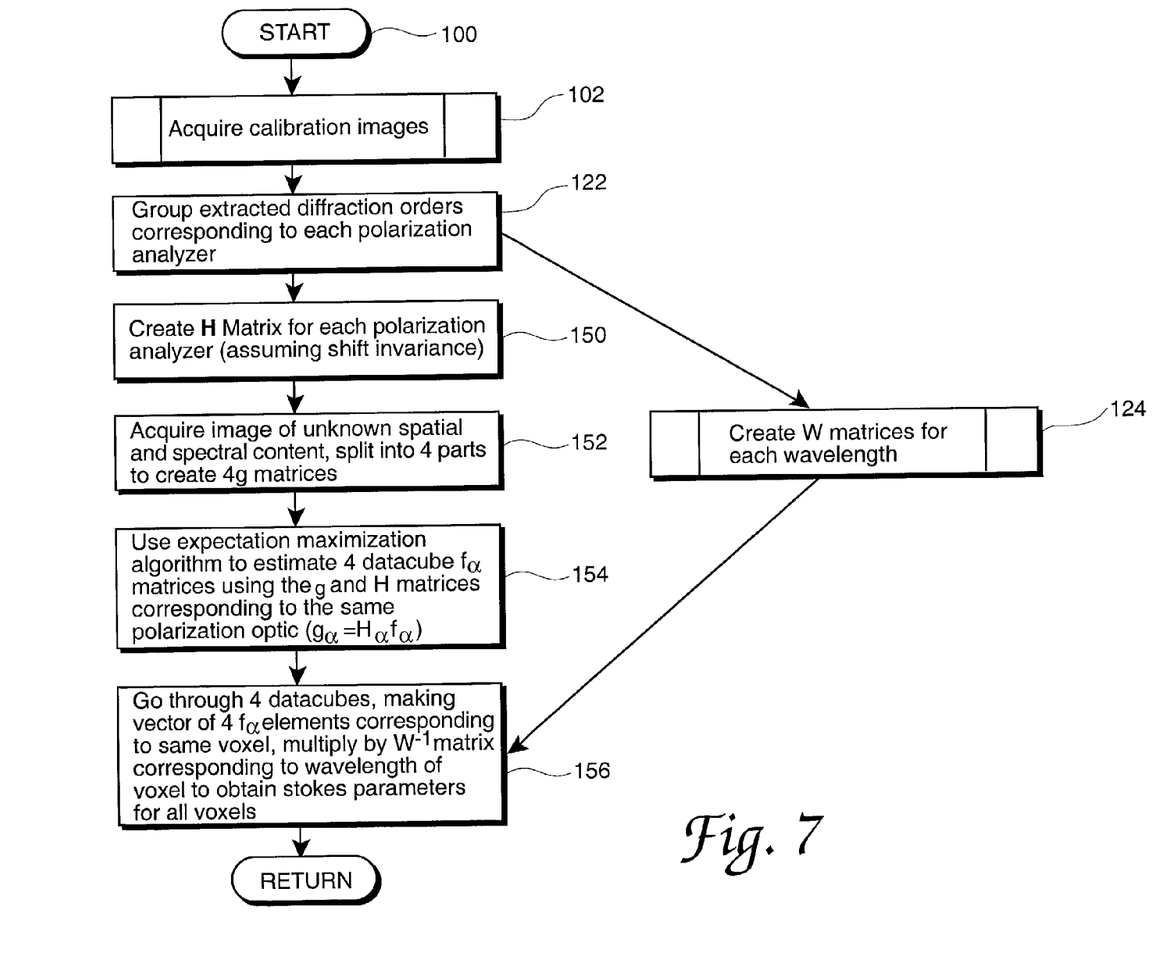
FIG. 7 is a sequence of operations, or routine, performed by the NS-CTISP of FIG. 4 to estimate the Stokes object cubes from the measured irradiance on the focal plane array.
Figure 8:
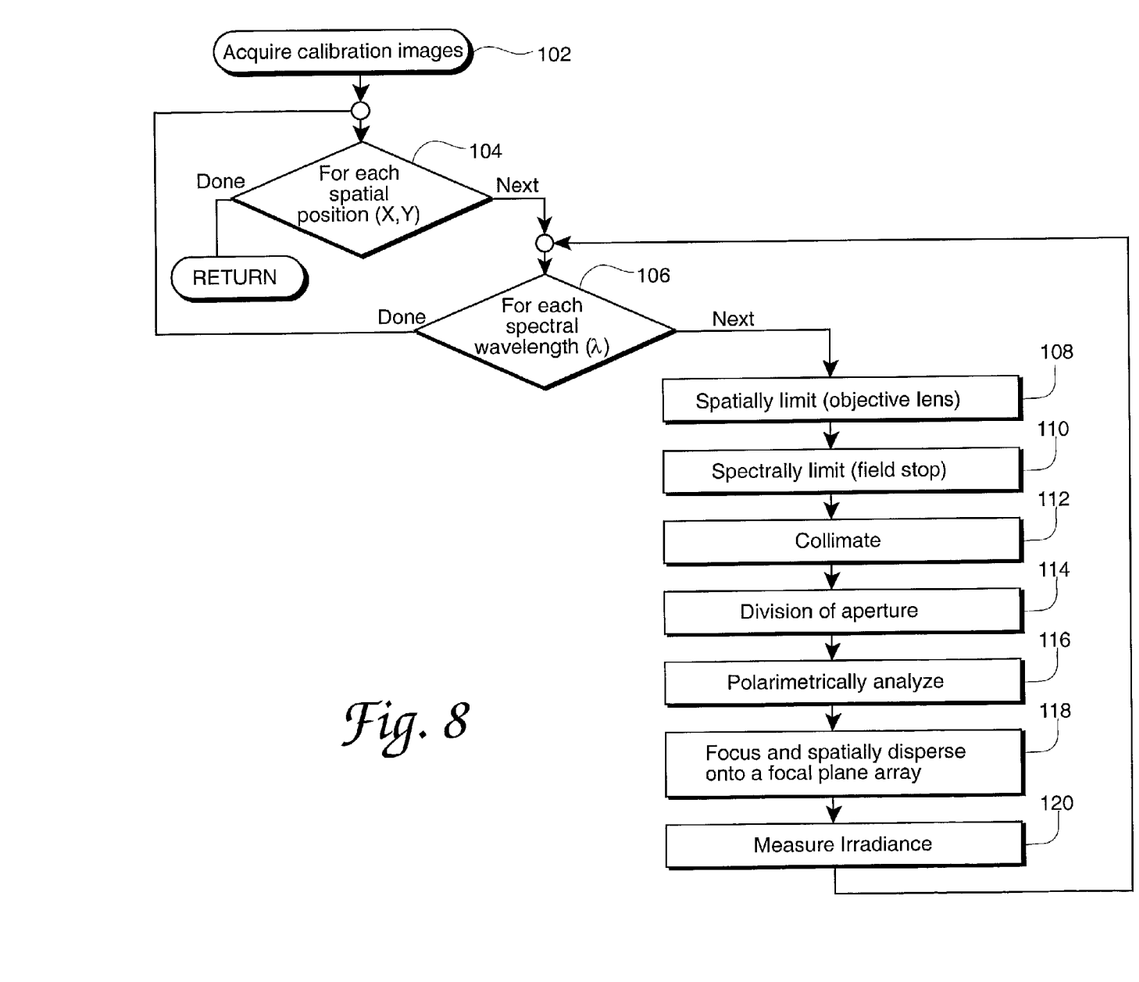
FIG. 8 is a sequence of operations referenced in the routine of FIG. 7 to calibrate the NS-CTISP.
Figure 9:
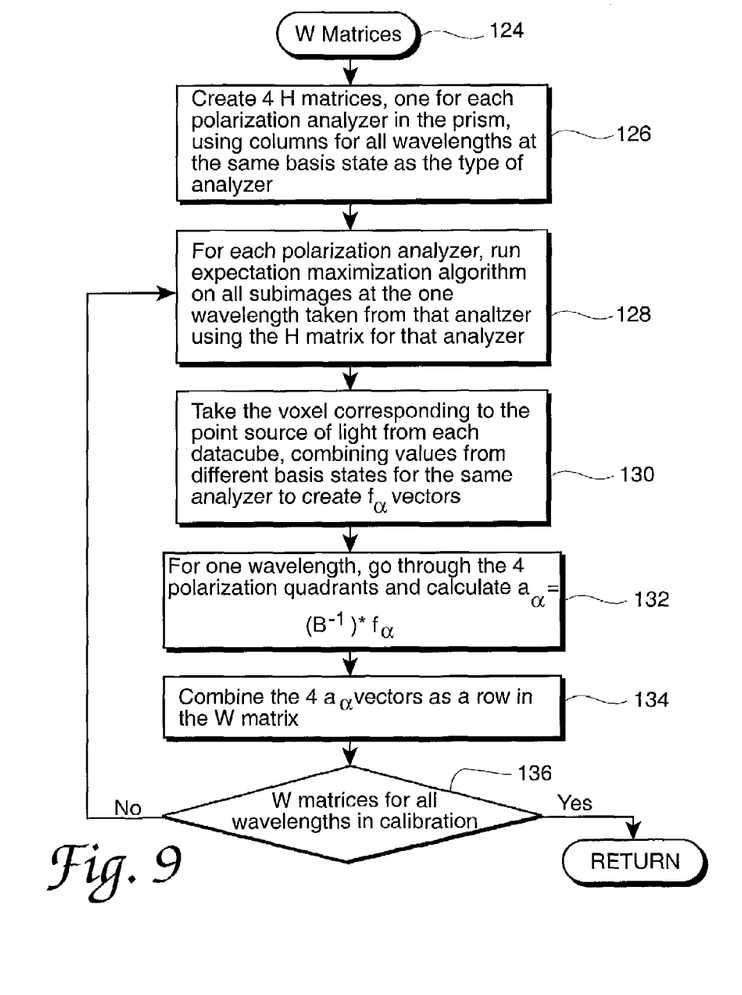
FIG. 9 is a sequence of operations referenced in the routine of FIG. 7 to create W matrices for using the calibration information for the NS-CTISP to analyze images of unknown spatial and spectral content.

In use, a sequence of operations, or routine 100, performed by the NS-CTISP 30 analyzes the complete polarization and spectral content of an image. With reference to FIGS. 7–9, the routine 100 begins by acquiring calibration images (block 102). In particular, spatial shift invariance is assumed in that calculating a shift mathematically yields the same results as physically moving a fiber optic calibration source anywhere in the camera field of view (FOV) for a point source of light of a constant wavelength and basis state. Each basis state is a light source having a pure polarization state, wherein the illustrative embodiments uses the basis states of vertical linear (VL), horizontal linear (HL), +45 degree linear (+45L) and right circular (RC) polarization.

With particular reference to FIG. 8, block 102 is described in additional detail, illustrating the optical processing performed on the calibration images. The calibration image is positioned for each spatial position (x,y), which entails only one x,y position when shift invariance is determined or assumed. First, a basis state is selected and the calibration is performed using each basis state (block 104). For each spatial position, each spectral wavelength is selected (block 106). The calibration image thus created (ΔxΔyΔλ) is optically processed in blocks 108–120: The calibration image is spectrally limited by a hot mirror and focused on a field stop (block 108). The field stop spatially limits the focused image (block 110). The image is then collimated (block 112) and separated into identical beams (i.e., division of aperture) (block 114). Each beam is polarimetrically analyzed (block 116). The individually analyzed beams are incident on a dispersive device for generate diffraction orders, which are then focused on a focal plane array (FPA) (block 118). The irradiances of the diffraction orders are then measured (block 120). Routine 100 returns back to block 106 for each wavelength. When each wavelength has been completed, block 106 returns to block 104 for any remaining spatial positions, which in turn returns to routine 100 of FIG. 7 when calibration for all basis states are complete.

Returning to FIG. 7, after the calibration images are optically processed, the measured irradiance is grouped into extracted diffraction orders corresponding to each polarization analyzer in the prism, thus ending up with four sub-images for each image (block 122). For each wavelength λ, a W matrix is created (block 124). With reference still to FIG. 8, creating W matrices (block 124) further includes creating four H matrices, one for each polarization analyzer in the prism, using columns with all wavelengths at the same basis state as the type of the analyzer (block 150). For example, the vertical analyzer combines all sub-images from the vertical analyzer that have basis state input of vertical polarization to form that H matrix. The same matrices used to create W matrices are also used when determining the spatial, spectral, and polarization content of unknown scenes.

FIG. 9 illustrates the calculations for creating the W matrices. For each polarization analyzer, the Expectation Maximization algorithm is executed on all sub-images at the one wavelength taken from that analyzer using the H matrix for that analyzer (block 128). In particular, Expectation Maximization is performed on four sub-images per analyzer, and thus on 16 total sub-images per wavelength. Then, values from each basis state corresponding to the same voxel are combined to create $f_\alpha$ vectors, thus creating four vectors with four elements each (block 130). Then, for one wavelength, go through the four polarization quadrants and calculate $a_\alpha = (B^{-1}) * f_\alpha$ where B is an array of the Stokes parameters for the known states of light given as inputs and f is a vector of the values measured at the different states for one optic (block 132). Then, the four $a_\alpha$ vectors are combined as a row in the W matrix as the final result for that wavelength (block 134). Then, a determination is made as to whether all of the W matrices have been created for all wavelengths used in the calibration (block 136). If not, block 136 returns to block 128 for the next wavelength, or else returns to routine 100 in FIG. 7.

In particular, in FIG. 7 after block 122, four H matrices were created assuming shift invariance, one H matrix for each polarization analyzer in the prism (block 150). These matrices, which were used to make the W matrices, are used again. An image is acquired having unknown spatial and spectral content, and is optically processed as described above for blocks 108–120; and the measured irradiance for the image is separated into four parts to create four g matrices (block 152). The Expectation Maximization algorithm is used to estimate the four data cube $f_\alpha$ matrices using the g and H matrices corresponding to the same polarization optic ($g_\alpha = H_\alpha f_\alpha$) (block 154). Each data cube is an array having dimensioned by the spatial (x,y) and wavelength (λ) for all voxels for the unknown scene.

Then, each of the four data cubes are processed by making a vector of the four corresponding $f_\alpha$ elements from each respective data cube for the same voxel. The resultant vector is multiplied by the inverse matrix $W^{-1}$ from block 124 for the selected wavelength of the voxel to obtain the Stokes parameters for all voxels (block 156).

By virtue of the foregoing, a non-scanning spectropolarimeter measures the complete received dynamically changing image, obtaining spectral and polarization content for each spatial position in the image.

Alternative, Variations and Substitutes

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. The invention in its broader aspects is, therefore, not limited to the specific details, representative apparatus and method, and illustrative examples shown and described. Accordingly, departures may be made from such details without departing from the spirit or scope of the general inventive concept.

For example, the CGH 64 can be any sort of dispersing element that provides simultaneous dispersion in more than one direction transverse to the optical axis 62. This includes single devices and single direction dispersion devices operating in series: (a) ruled and holographic gratings of both amplitude and phase type; (b) sets of crossed gratings of type listed in "a" above; (c) dispersive prisms and sets of crossed dispersive prisms; (d) dispersion by acousto-optic (AO) methods, multiple AO cells; (e) dispersion by spatial light modulators; (f) gratings constructed by MEMS devices; (g) dispersion by wire grids or other periodic metallic structures; (h) any binary or multilevel (phase levels) transmissive phase structure; (i) any reflective variant of the above, i.e. reflection rather than transmission gratings. It will be appreciated that the reflection variants of the above would likely result in a folded path or more complicated optical path than the illustrative embodiment of a non-scanning spectropolarimeter of FIG. 1.

As another example, the division of aperture approach illustrated by the tetrahedron prism 42 can be accomplished in other ways. For instance, U.S. Pat. No. 5,982,497 illustrates several methods of achieving both division of aperture and division of amplitude type systems. The division of amplitude type systems have more difficulty in removing instrumental polarization from the complete system however. The division of amplitude method can perform the same function and utilize either one or more FPAs 32 to collect the four sets of diffraction patterns 66. A logical choice is to use a single FPA 32 for each set of diffraction patterns.

As a further example, four sets of diffraction patterns, one for each "α", are needed as a minimum to determine the Stokes parameters; however, fewer sets can be obtained to obtain either linear or circular data alone, a subset of the Stokes vectors. More diffraction sets can be created by creating a greater number of division of aperture beams. In the case of the multifaceted prism, each prism face can have a different analyzer to improve on the polarimetric accuracy at the expense of the amount of light into each diffraction set.

As yet a further example, each diffraction set currently has 5 by 5 diffraction orders, any number of orders can work, with the fewest being two orthogonally dispersed orders up to an N by N array of orders where N can be an integer as large as is practical. As N increases, the spatial resolution in the field stop is reduced due to the required reduction of magnification of the field stop on the FPA. Lastly, the prism can be separated from the four polarization analyzers. In one embodiment, the tetrahedron prism contains no analyzers and a separate four quadrant polarization analyzer can be used in front of or behind the prism to achieve the same effect.

The invention therefore provides an improved non-scanning imaging spectropolarimeter. It is understood that modifications to the invention may be made as might occur to one with skill in the field of the invention within the scope of the appended claims. All embodiments contemplated hereunder that achieve the objects of the invention have therefore not been shown in complete detail. Other embodiments may be developed without departing from the spirit of the invention or from the scope of the appended claims.

We claim:

1. A spectropolarimeter, comprising:
   an input stage operably configured to collimate an image along an optical axis;
   a prismatic lense aligned with the optical axis and operably configured to perform division by refraction of the collimated image into a plurality of offset images;
   a plurality of polarization analyzers, each analyzer aligned with a respective one of a plurality of polarization states;
   a two-dimensional dispersive member preceeding the reimaging lens;
   a reimaging lens operable to reimage the analyzed plurality of offset and diffracted images; and
   a focal plane array to sense the diffraction images from the dispersive member.

2. The spectropolarimeter of claim 1, further comprising:
   a memory;
   a processor configured to perform a program resident in the memory, the program configured to calculate the complete polarization exitance for each voxel of the image.

3. A method of measuring complete spectral content of an image, the method comprising:
   collimating an image along an optical axis;
   performing division by refraction of the collimated image into four angularly offset images;
   polarization analyzing each offset image with a selected polarization state analyzer;
   two dimensionally diffractively dispersing the analyzed offset images and reimaging each analyzed and diffractively dispersed offset image onto a focal plane as a set of interleaved diffraction orders.

4. The method of claim 3, wherein the two dimensionally diffractively dispersing further comprises interleaving each set of polarization analyzed diffraction orders.

5. The method of claim 3, further comprising calculating the complete polarization exitance for each voxel of the image.

6. The method of claim 5, wherein calculating the complete polarization exitance for each voxel of the image further comprises:
   calibrating by measuring the set of diffraction orders in response to a calibration image having a known spatially-limited, spectrally-limited, and polarimetrically-limited content and by calculating a calibration matrix for each voxel;
   obtaining sets of diffraction orders from an image of unknown content;
   estimating a data cube for each polarization basis by use of the Expectation Maximization algorithm; and
   obtaining Stokes parameters for each voxel of the image by multiplying an inverse matrix of the calibration matrix corresponding to the selected voxel.

* * * * *